(12) United States Patent
Fiebig et al.

(10) Patent No.: US 7,241,450 B1
(45) Date of Patent: Jul. 10, 2007

(54) DNA SEQUENCE AND RECOMBINANT PRODUCTION OF A GRAMINEAE ALLERGEN

(75) Inventors: Helmut Fiebig, Schwarzenbek (DE); Roland Suck, Hamburg (DE); Oliver Cromwell, Wentorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/959,340

(22) PCT Filed: Apr. 12, 2000

(86) PCT No.: PCT/EP00/03259

§ 371 (c)(1), (2), (4) Date: May 29, 2002

(87) PCT Pub. No.: WO00/65060

PCT Pub. Date: Nov. 2, 2000

(30) Foreign Application Priority Data

Apr. 23, 1999 (DE) ................ 199 18 682

(51) Int. Cl.
*A61K 36/00* (2006.01)
*A61K 39/00* (2006.01)
*C07H 21/04* (2006.01)

(52) U.S. Cl. .............. 424/275.1; 530/370; 530/379; 536/23.6

(58) Field of Classification Search ............ 530/300, 530/868, 370; 424/275
See application file for complete search history.

(56) References Cited

U.S. PATENT DOCUMENTS 5,869,333 A * 2/1999 Singh et al. ............. 435/325

OTHER PUBLICATIONS

Suck et al., Journal of Immunological Methods, vol. 229, pp. 73-80, 1999.*
Lockey et al. Allergens and Allergen Immunotherapy. 2004. The Second Edition published by Marcel Dekker, Inc. pp. 37-50.*
Schramm et al. The Journal of Immunology. 1999. 162:2406-2414.*
Niogret et al.: Characterization of pollen polygal acturonase encoded by several cDNA clones in maize. Plant Molecular Biology, vol. 17, No. 6, Dec. 1991, pp. 1155-1164, XP002151351.
Suck et al.: Complementary DNA cloning and expression of a newly recognized high molecular mass allergen Phl p 13 from timothy grass (*Phleum pratense*) Clinical and Experimental Allergy, vol. 30, No. 3, Mar. 2000, pp. 324-332, XP000 953168.
Fisher et al.: Charaterization of Phl p4, a major timothy grass (*Phleum pratense*) pollen allergen, The Journal of Allergy and Clinical Immunology, vol. 98, No. 1, Jul. 1998, pp. 189-198, XP000953216.
Vrtala et al.: Immunologic characterization of purified recombinant timothy grass pollen (*Phleum pratense*) allergens (Phl p 1, Phl p2, Phl p5), The journal of allergy and clinical immunology, vol. 97, No. 3, Mar. 1996, pp. 781-787, XP000953173.

* cited by examiner

*Primary Examiner*—Phillip Gambel
*Assistant Examiner*—Chun Crowder
(74) *Attorney, Agent, or Firm*—Millen, White, Zelano, Branigan, P.C.

(57) ABSTRACT

The invention relates to the identification and characterization of a grass-pollen allergen, and to the recombinant DNA molecule encoding therefore, and to corresponding DNA and peptide sequences.

5 Claims, 2 Drawing Sheets

Figure 1: Nucleic acid sequence of p55

```
      GGGAAGAAGG AGGAGAAGAA GGAGGAGAAG AAGGAGAGTG
GAGATGCTGC GTCCGGGCC
      GACGGAACCT ACGACATCAC CAAGCTCGGC GCCAAACCCG
ACGGCAAGAC GGACTGCACC
      AAGGAGGTGG AGGAGGCATG GGCTTCGGCT TGCGGTGGTA
CCGGGAAGAA TACGATCGTC
      ATCCCCAAGG GTGATTTCCT GACCGGGCCT CTGAATTTCA
CCGGGCCATG CAAGGGCGAC
      AGCGTCACCA TCAAGCTGGA CGGCAACCTG CTGAGCTCCA
ACGACCTGGC CAAGTACAAG
      GCTAACTGGA TCGAGATCAT GCGGATCAAG AAACTCACTA
TCACCGGCAA AGGCACGCTC
      GACGGCCAAG GCAAGGCCGT GTGGGGCAAG AACAGCTGCG
CCAAGAACTA CAACTGCAAG
      ATCTTGCCAA ACACATTGGT GCTGGACTTC TGTGACGACG
CTCTCATCGA AGGCATCACC
      CTCCTAAACG CCAAGTTCTT CCATATGAAC ATCTACGAGT
GCAAGGGCGT GACCGTCAAG
      GACGTGACCA TCACCGCGCC CGGGGACAGC CCCAACACCG
ACGGCATCCA CATCGGCGAC
      TCGTCCAAGG TCACCATCAC CGACACCACC ATCGGCACCG
GCGACGACTG CATCTCCATC
      GGCCCCGGAA GCACCGGCCT CAACATCACC GGCGTGACCT
GCGGTCCAGG CCACGGCATC
      AGCGTTGGCA GCCTGGGACG GTACAAGGAC GAGAAGGACG
TGACCGACAT CACCGTAAAG
      AACTGCGTGC TCAAGAAGTC CACCAACGGC CTCCGGATCA
AGTCGTACGA GGACGCCAAG
      TCGCCGCTGA CGGCGTCGAA GCTGACCTAC GAGAACGTGA
AGATGGAGGA CGTGGGCTAC
      CCCATCATCA TCGACCAGAA GTACTGCCCC AACAAGATCT
GCACCTCCAA GGGAGACTCC
      GCCAGGGTCA CCGTCAAGGA CGTCACCTTC CGCAACATCA
CCGGCACCTC CTCCACCCCC
      GAGGCCGTCA GCCTGCTCTG CTCCGACAAG CAGCCCTGCA
ATGGTGTCAC CATGAACGAC
      GTCAAGATCG AGTACAGCGG CACCAACAAC AAGACCATGG
CTGTCTGCAC CAACGCCAAG
      GTCACCGCCA AGGGTGTCAG CGAGGCTAAC ACCTGCGCCG
CCTGATG
//
```

Figure 2: N-terminal amino acid sequence p55

GKKEEKKDEK KESGDAASXA

Figure 3: p55-specific primer

GGI AAI AAI GAI GAI AAI AAI GAI GA

Figure 4: Deduced amino acid sequence

SEQUENCE 395 AA; 41619 MW; 829349 CN;

GKKEEKKEEK KESGDAASGA DGTYDITKLG AKPDGKTDCT KEVEEAWASA
CGGTGKNTIV
IPKGDELTGP LNFTGPCKED SVTIKLDGNL LSSNDLAKYK ANWIEIMRIK
KLTITGKGTL
DGQGKAVWGK NSCAKNYNCK ILPNTLVLDF CDDALIEGIT LLNAKFFHMN
IYECKGVTVK
DVTITAPGDS PNTDGIHIGD SSKVTITDTT IGTGDDCISI GPGSTGLNIT
GGACGPGHGI
SVGSLGRYKD EKDVTDITVK NCVLKKSTNG LRIKSYEDAK SPLTASKLTY
ENVKMEDVGY
PIIIDQKYCP NKICTSKGDS ARVTVKDVTF RNITGTSSTP RAVSLLCSDK
QPCNGVTMND
VKIEYSGTNN KTMAVCTNAK VTAKGVSEAN TCAA*

DNA SEQUENCE AND RECOMBINANT PRODUCTION OF A GRAMINEAE ALLERGEN

The invention relates to the identification and characterisation of a grass-pollen allergen and of the recombinant DNA molecule encoding therefor. The pollen of *Phleum pratense* serve as natural raw material. The invention also covers fragments, partial sequences and mutants. The recombinant DNA molecules and the derived polypeptides, fragments or variants can be used for the therapy of pollen-allergy illnesses. Furthermore, the proteins and fragments produced by recombinant methods can be used for the diagnosis of pollen allergies.

Allergies of type 1 are of worldwide importance. Up to 20% of the population in industrialised countries suffers from complaints such as allergic rhinitis, conjunctivitis or bronchial asthma. These allergies are caused by allergens present in the air (aeroallergens), which are released by sources of various origin, such as plant pollen, mites, cats or dogs. Up to 40% of these type 1 allergy sufferers in turn exhibit specific IgE reactivity in the case of grass pollen (Friedhoff et al., 1986, J Allergy Clin. Immunol. 78, 1190-201).

The substances which trigger type 1 allergies are proteins, glycoproteins or polypeptides. After uptake via the mucous membranes, these allergens react with the IgE molecules bonded to the surface of mast cells in sensitised persons. If two IgE molecules link up with one another through an allergen, this results in the release of mediators (for example histamine, prostaglandins) and cytokines by the effector cells and thus in the corresponding clinical symptoms.

Depending on the relative frequency of the allergy sufferer having IgE antibodies against certain allergens, a distinction is made between major and minor allergens. In the case of timothy grass (*Phleum pratense*), Phl p 1 (Petersen et al., 1993, J. Allergy Clin. Immunol. 92, 789-796), Phl p 5 (Matthiesen and Löwenstein, 1991, Clin. Exp. Allergy 21, 297-307; Petersen et al., 1992), Phl p 6 (Petersen et al., 1995, Int. Arch. Allergy Immunol. 108, 49-54) and Phl p 2/3 (Dolecek et al., 1993, FEBS 335 (3), 299-304) have hitherto been characterised as major allergens and Phl p 4 (Löwen-stein, 1978, Prog. Allergy 25, 1-62) and groups 10 and 11 from *Lolium perenne* (Ansari et al., 1987, J. Allergy Clin. Immunol. 80, 229-235) as minor allergens.

In connection with the present invention, the allergen Phl p 4 is of particular importance since it has a similar molecular weight of about 55 kDa (Fischer et al., 1996, J. Allergy Clin. Immunol. 98 (1), 189-98) to the new allergen and is thus the most readily comparable with the allergen produced in accordance with the invention, but differs significantly in immunological and biochemical terms. In contrast to the other allergens mentioned above, Phl p 4 is the only one whose genomic or transcriptive (cDNA) sequence has not yet been identified. Sequence data are available, inter alia, for Phl p 1 (Laffer et al., 1994, J. Allergy Clin. Immunol. 94, 1190-98; Petersen et al., 1995, J. Allergy Clin. Immunol. 95 (5), 987-994), Phl p 5 (Vrtala et al., 1993, J. Immunol. 151 (9), 4773-4781), Phl p 6 (Petersen et al., 1995, Int. Arch. Allergy Immunol. 108 (1), 55-59) and Phl p 2 (Dolecek et al., 1993, FEBS 335 (3), 299-304). With the aid of cDNA sequences, it is possible to produce recombinant allergens which can be used in diagnostics and therapy (Scheiner and Kraft, 1995, Allergy 50, 384-391).

A classical approach to effective therapeutic treatment of allergies is specific immunotherapy or hyposensitisation (Fiebig, 1995, Allergo J. 4 (6), 336-339, Bousquet et al., 1998, J. Allergy Clin. Immunol. 102 (4), 558-562). In these methods, natural allergen extracts are injected subcutaneously into the patient in increasing doses. However, this method entails the risk of allergic reactions or even anaphylactic shock. In order to minimise these risks, innovative preparations in the form of allergoids are being employed. These are chemically modified allergen extracts which have significantly reduced IgE reactivity, but identical T-cell reactivity compared with the untreated extract (Fiebig, 1995, Allergo J. 4 (7), 377-382).

An even greater degree of therapy optimisation would be possible with allergens produced by recombinant methods. Defined cocktails of high-purity allergens produced by recombinant methods, if desired matched to individual patients, could supersede extracts from natural allergen sources since the latter, in addition to the various allergens, contain a relatively large number of immunogenic, but non-allergenic accompanying proteins. Realistic perspectives which could result in safe hyposensitisation with expression products are offered by specifically mutated recombinant allergens in which IgE epitopes are specifically deleted without impairing the T-cell epitopes which are essential for the therapy (Schramm et al., 1999, J. Immunol. 162, 2406-2414).

Another possibility for influencing the disturbed Th-cell balance in allergy sufferers by therapeutic methods is treatment with expressable DNA which encodes for the relevant allergens. Initial experimental confirmation of the allergen-specific effect on the immune response has been obtained in rodents by injection of allergen-encoding DNA (Hsu et al., 1996, Nature Medicine 2 (5), 540-544).

The invention can advantageously be used in in-vitro and in-vivo diagnostics of allergic illnesses, especially of pollinosis. To this end, the cloned nucleic acid is ligated in an expression vector, and this construct is expressed in a suitable cell type. After biochemical purification, this recombinant allergen is available for the detection of IgE antibodies by established methods. On the other hand, the invention can also be used as an essential component in a recombinant allergen-containing or nucleic acid-containing preparation for specific immunotherapy. Numerous possibilities present themselves here. Firstly, the protein with an unmodified primary structure may be a constituent of the preparation. Secondly, through specific deletion of IgE epitopes of the entire molecule or the production of individual fragments which encode for T-cell epitopes, a hypoallergenic (allergoid) form can be used for in accordance with the invention for therapy in order to avoid undesired side-effects. Finally, through the nucleic acid per se, if it is ligated with a eucaryontic expression vector, a preparation is produced which, when applied directly, modifies the allergic immune state in the therapeutic sense.

BRIEF DESCRIPTION OF THE DRAWINGS

FIG. 1: Nucleic acid sequence of p55 (SEQ ID NO:1)

FIG. 2: N-terminal amino acid sequence of p55 (SEQ ID NO:2)

FIG. 3: p-55 specific primer (SEQ ID NO:3)

FIG. 4: Deduced amino acid sequence (SEQ ID NO:4)

The invention relates to a recombinant DNA molecule which consists of a nucleic acid sequence (FIG. 1) and encodes for an allergen. Pollen grains of the Graminae, such as, for example, *Phleum pratense, Lolium perenne, Dactylis glomerata, Poa pratensis, Cynodon dactylon, Holcus lanatus*, inter alia, serve as natural raw material.

After purification and isolation of the natural allergen, N-terminal protein sequencing is carried out. Based on the nucleic acid sequence deduced therefrom, a primer is produced. With the aid of this primer, the corresponding cDNA was obtained from a cDNA population of pollen by means of PCR, cloned and characterised. Fragments and partial sequences were produced in accordance with the invention from this DNA molecule encoding for an allergen.

After expression of the recombinant DNA molecule or the fragments and partial sequences by means of suitable expression vectors in cellular systems, the allergen or the hypoallergenic variants or fragments were purified.

The purification of natural allergen from timothy grass pollen was carried out in a two-step process. After aqueous extraction of pollen, the resultant extract was separated into two fractions, the fraction passing through the column and the eluate, by means of hydrophobic interaction chromatography. The fraction passing through the column contained three allergens, Phl p 1 (30-35 kDa), Phl p 2/3 (11-14 kDa), and an unknown allergen (55-60 kDa). These proteins were separated from one another by gel filtration using Superdex 75.

This hitherto unknown allergen (working name p55) was separated off by means of SDS-PAGE, subsequently blotted onto a PVDF membrane, and a precisely defined fraction isolated. An N-terminal amino acid sequence was determined from this p55 molecule by Edman degradation (FIG. 2).

For the production and cloning of the corresponding cDNA of p55, a specific DNA primer (21mer) based on the N-terminal sequence (FIG. 3) was constructed in accordance with the invention. The second primer used was an anchor sequence which was localised in the oligo-dT primer used for reverse transcription. A PCR reaction was carried out under stringent conditions with a cDNA produced from the representative mRNA population from *Phleum pratense* pollen and the primer according to the invention and the anchor primer. In analytical gel electrophoresis of the PCR reaction, an amplified DNA having a size of 1.65 kb was identified. This amplified DNA was ligated in a pCR2.1 vector and successfully transformed. Sequencing of the inserts from two different clones gave the identical sequence.

In this primary amplified DNA, an open reading frame (ORF) of 1492 bp (see FIG. 1) was identified.

In order to produce the corresponding recombinant protein (FIG. 4) from this nucleic acid, re-cloning of the pCR2.1 vector by means of restriction enzymes into the expression vector pProEx Htb was firstly carried out. After expression and biochemical purification of the expression product, a number of analyses of the allergenic nature of the developed protein were carried out. In all the analyses, for example Western blot and dot blot, the recombinant protein reacted specifically with IgE from the patients which had diagnosed clinical symptoms of grass-pollen allergy. The control used was the natural p55. Accordingly, the recombinant protein is clearly an allergen. This expression product thus serves for highly specific, improved diagnosis of grass-pollen allergy sufferers.

With the intention of producing hypoallergenic variants for improved therapeutic use, defined fragments and combinations of partial sequences were developed in accordance with the invention starting from the nucleic acid cloned in the expression vector. In addition, site-specific point mutations were introduced, predominantly at the triplet encoding for cysteine. This part of the invention is thus distinguished from the invention developed for diagnostic purposes through reduced or absent IgE reactivity. Preparations which have clearly low or absent side effects owing to reduced [lacuna] are thus available for hyposensitisation. If the nucleic acids encoding for hypoallergenic protein variations or the unmodified nucleic acid encoding for p55 are ligated with a human expression vector, these constructs can likewise be used as preparations for specific immunotherapy.

The invention is thus a) a recombinant DNA molecule which contains a nucleotide sequence which encodes for a polypeptide which acts as allergen and is preferably expressed by Gramineae (Poaceae) and monocotyledon plants;

b) a DNA molecule as indicated having a nucleotide sequence which originates from *Phleum pratense;* c) a nucleotide sequence of the indicated DNA molecule as shown in FIG. 1;

d) a DNA molecule which has a nucleotide sequence which hybridises with the last-mentioned nucleotide sequence defined in FIG. 1;

e) partial sequences and combinations of partial sequences which are present in the nucleotide sequence according to c) or d);

f) a DNA molecule which contains a nucleotide sequence a)-d) which is modified by specific mutations of individual codons and elimination or addition;

g) a nucleotide sequence according to c) which encodes for an immunomodulatory T-cell reactive fragment;

h) a nucleotide sequence according to d) which encodes for an immunomodulatory T-cell reactive fragment;

i) a nucleotide sequence according to e) which encodes for an immunomodulatory T-cell reactive fragment;

j) a nucleotide sequence according to f) which encodes for an immunomodulatory T-cell reactive fragment;

k) a recombinant DNA expression vector or a cloning system consisting of the recombinant DNA molecule defined in a)-d) functionally connected to an expression control sequence;

l) a polypeptide which is encoded from nucleic acid according to c);

m) a polypeptide which is encoded from nucleic acid according to d);

n) a polypeptide which is encoded from nucleic acid according to e);

o) a polypeptide which is encoded from nucleic acid according to f);

p) a polypeptide which is encoded from nucleic acid according to g);

q) a polypeptide which is encoded from nucleic acid according to h);

r) a polypeptide which is encoded from nucleic acid according to i);

s) a polypeptide which is encoded from nucleic acid according to j);

t) a method for the production of a polypeptide, a fragment or derivative thereof by cultivation of procaryontic or eucaryontic cells which have been transformed with an expression vector according to claim 11, and the isolation of the corresponding protein or polypeptide from the culture;

u) a method for the diagnosis of pollen allergies in vivo or in vitro using the polypeptides according to l)-n);

v) a pharmaceutical preparation which comprises a polypeptide, fragment or derivative according to l)-t) for the therapeutic treatment of pollen-allergic humans or animals;

w) a method for the therapy of pollen-allergic humans or animals using the pharmaceutical preparation defined in v);

x) a method for the therapy of pollen allergies by DNA vaccination with constructs defined in k);

y) a method for the therapy of pollen allergies by DNA vaccination with the vectors defined in k) which contain immunostimulatory DNA fragments.

The invention thus serves to improve in-vitro diagnostics as part of identification of the patient-specific sensitisation spectrum which resolves allergen components. The invention likewise serves for the production of significantly improved preparations for the specific immunotherapy of grass-pollen allergy sufferers.

The invention claimed is:

1. An isolated polypeptide which comprises the amino acid sequence set forth in SEQ ID NO:4.
2. An isolated polypeptide which is encoded by the polynucleotide of SEQ ID NO:1.
3. A composition which comprises the polypeptide according to claim 1.
4. The isolated polypeptide of claim 1, wherein said polypeptide is the natural allergen isolated from *Phleum pratense*.
5. The isolated polypeptide of claim 1, wherein said polypeptide is recombinant.

* * * * *

SEQUENCE LISTING

```
<160> NUMBER OF SEQ ID NOS: 4

<210> SEQ ID NO 1
<211> LENGTH: 1187
<212> TYPE: DNA
<213> ORGANISM: Unknown Organism
<220> FEATURE:
<223> OTHER INFORMATION: Description of Unknown Organism: Gramineae
      allergen nucleic sequence

<400> SEQUENCE: 1
gggaagaagg aggagaagaa ggaggagaag aaggagagtg gagatgctgc gtccggggcc      60
gacggaacct acgacatcac caagctcggc gccaaacccg acggcaagac ggactgcacc     120
aaggaggtgg aggaggcatg ggcttcggct tgcggtggta ccgggaagaa tacgatcgtc     180
atccccaagg gtgatttcct gaccgggcct ctgaatttca ccgggccatg caagggcgac     240
agcgtcacca tcaagctgga cggcaacctg ctgagctcca acgacctggc caagtacaag     300
gctaactgga tcgagatcat gcggatcaag aaactcacta tcaccggcaa aggcacgctc     360
gacggccaag gcaaggccgt gtggggcaag aacagctgcg ccaagaacta caactgcaag     420
atcttgccaa acacattggt gctggacttc tgtgacgacg ctctcatcga aggcatcacc     480
ctcctaaacg ccaagttctt ccatatgaac atctacgagt gcaagggcgt gaccgtcaag     540
gacgtgacca tcaccgcgcc cggggacagc cccaacaccg acggcatcca catcggcgac     600
tcgtccaagg tcaccatcac cgacaccacc atcggcaccg cgacgactg catctccatc      660 ggccccggaa gcaccggcct caacatcacc ggcgtgacct gcggtccagg ccacggcatc     720
agcgttggca gcctgggacg gtacaaggac gagaaggacg tgaccgacat caccgtaaag     780
aactgcgtgc tcaagaagtc caccaacggc ctccggatca agtcgtacga ggacgccaag     840
tcgccgctga cggcgtcgaa gctgacctac gagaacgtga agatggagga cgtgggctac     900
cccatcatca tcgaccagaa gtactgcccc aacaagatct gcacctccaa gggagactcc     960
gccagggtca ccgtcaagga cgtcaccttc cgcaacatca ccggcacctc ctccacccc     1020 gaggccgtca gcctgctctg ctccgacaag cagccctgca atggtgtcac catgaacgac     1080
gtcaagatcg agtacagcgg caccaacaac aagaccatgg ctgtctgcac caacgccaag     1140
gtcaccgcca agggtgtcag cgaggctaac acctgcgccg cctgatg                    1187

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:
      Illustrative p55 N-terminal sequence
<220> FEATURE:
```

```
<221> NAME/KEY: MOD_RES
<222> LOCATION: (19)
<223> OTHER INFORMATION: Variable amino acid

<400> SEQUENCE: 2

Gly Lys Lys Glu Glu Lys Lys Asp Glu Lys Lys Glu Ser Gly Asp Ala
 1               5                  10                  15

Ala Ser Xaa Ala
            20

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (24)
<223> OTHER INFORMATION: i

<400> SEQUENCE: 3
ggnaanaang anganaanaa nganga                                          26

<210> SEQ ID NO 4
<211> LENGTH: 394
<212> TYPE: PRT
<213> ORGANISM: Unknown Organism
<220> FEATURE:
<223> OTHER INFORMATION: Description of Unknown Organism: Gramineae
      allergen protein sequence

<400> SEQUENCE: 4

Gly Lys Lys Glu Glu Lys Lys Glu Glu Lys Lys Glu Ser Gly Asp Ala
 1               5                  10                  15

Ala Ser Gly Ala Asp Gly Thr Tyr Asp Ile Thr Lys Leu Gly Ala Lys
            20                  25                  30

Pro Asp Gly Lys Thr Asp Cys Thr Lys Glu Val Glu Glu Ala Trp Ala
        35                  40                  45

Ser Ala Cys Gly Gly Thr Gly Lys Asn Thr Ile Val Ile Pro Lys Gly
    50                  55                  60
```

-continued

```
Asp Phe Leu Thr Gly Pro Leu Asn Phe Thr Gly Pro Cys Lys Gly Asp
 65                  70                  75                  80

Ser Val Thr Ile Lys Leu Asp Gly Asn Leu Leu Ser Ser Asn Asp Leu
                 85                  90                  95

Ala Lys Tyr Lys Ala Asn Trp Ile Glu Ile Met Arg Ile Lys Lys Leu
            100                 105                 110

Thr Ile Thr Gly Lys Gly Thr Leu Asp Gly Gln Gly Lys Ala Val Trp
        115                 120                 125

Gly Lys Asn Ser Cys Ala Lys Asn Tyr Asn Cys Lys Ile Leu Pro Asn
    130                 135                 140

Thr Leu Val Leu Asp Phe Cys Asp Ala Leu Ile Glu Gly Ile Thr
145                 150                 155                 160

Leu Leu Asn Ala Lys Phe Phe His Met Asn Ile Tyr Glu Cys Lys Gly
                165                 170                 175

Val Thr Val Lys Asp Val Thr Ile Thr Ala Pro Gly Asp Ser Pro Asn
            180                 185                 190

Thr Asp Gly Ile His Ile Gly Asp Ser Ser Lys Val Thr Ile Thr Asp
        195                 200                 205

Thr Thr Ile Gly Thr Gly Asp Asp Cys Ile Ser Ile Gly Pro Gly Ser
    210                 215                 220

Thr Gly Leu Asn Ile Thr Gly Gly Ala Cys Gly Pro Gly His Gly Ile
225                 230                 235                 240

Ser Val Gly Ser Leu Gly Arg Tyr Lys Asp Glu Lys Asp Val Thr Asp
                245                 250                 255

Ile Thr Val Lys Asn Cys Val Leu Lys Ser Thr Asn Gly Leu Arg
            260                 265                 270

Ile Lys Ser Tyr Glu Asp Ala Lys Ser Pro Leu Thr Ala Ser Lys Leu
        275                 280                 285

Thr Tyr Glu Asn Val Lys Met Glu Asp Val Gly Tyr Pro Ile Ile Ile
    290                 295                 300

Asp Gln Lys Tyr Cys Pro Asn Lys Ile Cys Thr Ser Lys Gly Asp Ser
305                 310                 315                 320

Ala Arg Val Thr Val Lys Asp Val Thr Phe Arg Asn Ile Thr Gly Thr
                325                 330                 335

Ser Ser Thr Pro Glu Ala Val Ser Leu Leu Cys Ser Asp Lys Gln Pro
            340                 345                 350

Cys Asn Gly Val Thr Met Asn Asp Val Lys Ile Glu Tyr Ser Gly Thr
        355                 360                 365

Asn Asn Lys Thr Met Ala Val Cys Thr Asn Ala Lys Val Thr Ala Lys
    370                 375                 380

Gly Val Ser Glu Ala Asn Thr Cys Ala Ala
385                 390
```